United States Patent [19]

Bargeton et al.

[11] 4,005,702
[45] Feb. 1, 1977

[54] SYSTEM AND METHOD FOR EXPLORATION OF THE INTRATHORACIC VENTILATORY MECHANISM

[75] Inventors: Daniel Ernest Louis Bargeton; P. Vaida, both of Paris; G. Vardon, Neuilly Plaisance, all of France

[73] Assignee: Institut National de la Sante et de la Recherche Medical, France

[22] Filed: May 22, 1975

[21] Appl. No.: 579,971

[30] Foreign Application Priority Data

May 22, 1974 France .............................. 74.17785

[52] U.S. Cl. ............................................. 128/2.08
[51] Int. Cl.$^2$ ........................................ A61B 5/08
[58] Field of Search .......... 128/2.08, 2.07, DIG. 29

[56] References Cited
UNITED STATES PATENTS

| | | | |
|---|---|---|---|
| 3,480,006 | 11/1969 | Schomber | 128/2.08 |
| 3,902,481 | 9/1975 | Bargeton et al. | 128/2.08 |

OTHER PUBLICATIONS

Comroe, et al., "Design of Body Plethys. for Studying Cardio. Physiology", J. of App. Phys., vol. 14, 1959, May, pp. 439–444.
Dubois et al., "Method for Measuring Airway Resist. in Man Using Body Plethys.", J. of Clinical Investigation, vol. 35, 1956, pp,. 327–335.
Gulesian, "Instr. for Measurement of MEFV Parameters", IEEE Trans. on Bio–Med. Eng., Sept. 1971, pp. 378–382.
Jaeger et al., "Meas. of Airway Resist. . . . Body Plethys.", J. of App. Phys., vol. 19, No. 4, July 1964, pp. 813–820.

Primary Examiner—Robert W. Michell
Assistant Examiner—Lee S. Cohen
Attorney, Agent, or Firm—Craig & Antonelli

[57] ABSTRACT

The invention relates to a system and method for the exploration of the intrathoracic ventilatory mechanism which employs a signal y formed according to the equation:

$$y = \lambda_1 V + \lambda_2 \frac{dV}{dt} + Pp + \lambda_3$$

in which $V$ is the volume displaced in the mouth, $dV/dt$ is the first derivative of V with respect to the time, $Pp$ is the pleural pressure given by an oesophageal gas-bag, and $\lambda_1$, $\lambda_2$, $\lambda_3$ are three adjustable parameters. The signal y is displayed on an oscilloscope as a loop which is a function of the volume V, and potentiometers corresponding to $\lambda_1$, $\lambda_2$, $\lambda_3$ are adjusted to determine the value of the parameters. First, the potentiometers for $\lambda_2$ are adjusted to cause the loop to close in a straight line, then the potentiometers for $\lambda_1$ are adjusted until this straight line is horizontal, and subsequently the potentiometers for $\lambda_3$ are adjusted until this straight line lies over the x axis. Therefore the values given to the parameters are $\lambda_2 = R$ intrathoracic resistance, $\lambda_1 = E$ intrathoracic elastance, and $\lambda_3 = E(Vo - Vr)$ where $Vo$ is the pulmonary volume at the beginning of the inhalation and $Vr$ the relaxation volume.

19 Claims, 1 Drawing Figure

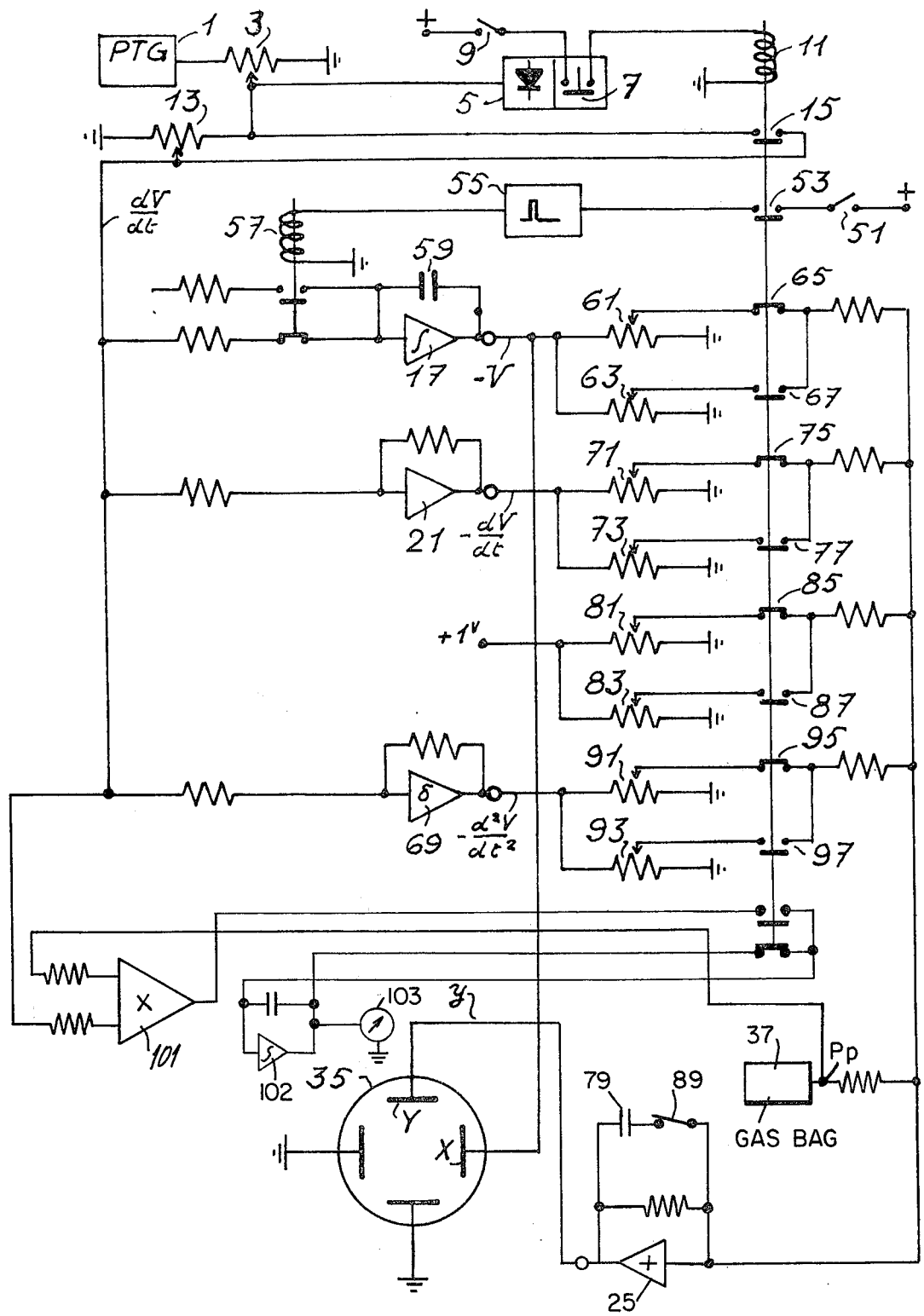

SYSTEM AND METHOD FOR EXPLORATION OF THE INTRATHORACIC VENTILATORY MECHANISM

The present invention relates to a system and method for exploration of the intrathoracic ventilatory mechanism. In particular, the present invention is an improvement of the system and method disclosed in copending commonly assigned patent application Ser. No. 454,711, filed Mar. 25, 1974, now U.S. Pat. No. 3,902,481, the disclosure of which is incorporated herein.

The copending application relates to a system and method for exploration of the intrathoracic ventilatory mechanism wherein an oscilloscope is supplied with a signal formed according to the equation $$y = V + \lambda \frac{dV}{dt},$$

wherein $V$ is the volume displaced in the mouth of a patient and $\lambda$ is an adjustable parameter. The present invention relates to an improvement of this system and method wherein other adjustable parameters are incorporated in the signal and the other adjustable parameters represent, for example the pleural pressure and the inertance.

The present invention utilizes the following equation which corresponds to the equation of the copending application:

$$E(Vp - Vr) + R \frac{dVp}{dt} + Pp = 0 \qquad (1)$$

wherein:

$E$ is the intrathoracic elastance;
$R$ is the intrathoracic resistance;
$Pp$ is the pleural pressure (given by an oesophageal balloon with $Pp = -\Delta p$ motor pressure developed by the respiratory muscles as in the copending application;)
$Vp$ is the pulmonary volume; and
$Vr$ is the relaxation volume.

Also, the copending application and the present invention consider the volume displaced in the mouth or inhaled volume $V$ and the pulmonary volume at the beginning of the inhalation $Vo$ in accordance with the relation:

$$Vp = Vo + V \qquad (2)$$

from which there results the equation:

$$EV + R \frac{dV}{DT} + Pp + E(Vo - Vr) = 0 \qquad (3)$$

However, the present invention in addition considers a signal $y$ which is an improvement over the signal $y$ of the copending application in that the signal is formed according to the equation:

$$y = \lambda_1 V + \lambda_2 \frac{dV}{dt} + Pp + \lambda_3 \qquad (4)$$

where $y$ is given by circuit supplied with $dV/dt$ from a pneumotachograph, $Pp$ is furnished by an oesophageal sonde, the parameters $\lambda_1, \lambda_2, \lambda_3$ are provided by three potentiometers, from which there results:

$$y = (\lambda_1 - E) V + (\lambda_2 - R) \frac{dV}{Dt} + \lambda_3 - E(Vo - Vr) \qquad (5)$$

which signal is displayed as a function of the inhaled volume $V$ on an oscilloscope of the type having a long persistence screen or with XY axes.

In order to employ the system and method according to the present invention, the signal y is displayed and first the parameters $\lambda$ are set to zero which constitutes a calibrating position and gives the measurement of the intrathoracic ventilatory work W by the surface area of the displayed loop. Then the parameter $\lambda_2$ is successively adjusted until the loop is closed in a straight line, the parameter $\lambda_1$ is adjusted so that the line becomes horizontal, and then the parameter $\lambda_3$ is adjusted to bring the straight line to lie upon the $x$ axis. After adjusting the parameters of equation (5) which parameter values are determined by the potentiometer settings, there results:

$$\lambda_2 = R \quad \lambda_1 = E \quad \lambda_3 = E(Vo - Vr).$$

The system and method according to the present invention presents the following advantages:

the determination of the intrathoracic elastance E and of the intrathoracic resistance R by a zero method which requires only one qualitative observation from the oscilloscope and does not require any graphical calibrating;

the main component of the noise which is relatively important on account of the parasitic signals of cardiac origin (as described in the copending application), is parallel ot the axis of $y$ and can be filtered (by a very simple filtering method) without distortion of the signal;

the signal being identically nulled so that a big amplifying gain can be employed without saturation thereby providing the best observation conditions;

as in the copending application, it is possible and easy to observe separately the inhalation and the exhalation of each cycle.

The system and method according to the present invention due to its high sensitivity and to the above-mentioned filtering also permits the determination of the inertance. It is generally stated that the inertia plays an unimportant role during most of the respiratory cycle of the patient, but it is not the same at the beginning of the inhalation and at the beginning of the exhalation which have a discontinuous character, and at the hyperpnea of the exercise of the muscles. According to another feature of the present invention, the signal y also includes an additional adjustable parameter and the above-mentioned equations (1) (4) (5) become respectively:

$$E(Vp - Vr) + R \frac{dVp}{dt} + L \frac{d^2 Vp}{dt^2} + Pp = O \qquad (1B)$$

(wherein $L$ is the intrathoracic inertance)

$$y = \lambda_1 V + \lambda_2 \frac{dV}{dt} + \lambda_4 \frac{d^2V}{dt^2} + Pp + \lambda_3 \qquad (4b)$$

$$y = (\lambda_1 - E) V + (\lambda_2 - R) \frac{dV}{dt} + (\lambda_4 - L) \frac{d^2V}{dt^2} + (\lambda_3 - E)(Vo - Vr) \qquad (5b)$$

The above-mentioned use of the system according to the present invention is very easily completed, after controlling $\lambda_1$, $\lambda_2$, $\lambda_3$ as indicated above (which are not modified by the very weak role or unimportant role of the inertia during the greater part of the cycle), by the control of $\lambda_4$.

The system according to the present invention also presents the advantage that apart of its normal utilization, i.e. directly on the patient, the signals of $dV/Dt$ and $Pp$ may be recorded, for example on magnetic tape. This immobilizes the patient only for a short time which is very much appreciated with certain illnesses, and also allows the determination of all the parameters on each of the registered cycles, and therefore the statistic interpretation of the data.

These and other objects, features and changes of the present invention will become more apparent from the following description when taken in connection with the accompanying single FIGURE of the drawing, which shows for purposes of illustration only, a single figure which is a schematic circuit arrangement in accordance with the present invention.

As shown in the FIGURE and as disclosed in the copending application there is provided a system arrangement including a pneumotachograph 1, a potentiometer 3 for regulating the gain, a circuit 5 for detecting the sign of $dV/dt$ including a work contact 7 and a switch 9 and its associated relay 11, a potentiometer 13 for the correction of the gain upon exhalation, an integrator-inverter 17 furnishing the signal $-V$, an amplifier-inverter 21 furnishing the signal $-dV/dt$, a gas-bag 37 furnishing the signal $Pp$, the inverter summing means 25 furnishing the signal y to the vertical active plate Y of an oscilloscope 35. Also, according to the present invention, there is provided a switch 51, which when closed, supplies power by a contact means 53 of the relay 11 to a pulse generator 55 which provides pulses of a duration of 50 ms to a relay 57 so as to discharge the capacitor 59 in the feedback loop of the integrator 17. It is noted that this resetting of the integrator 17 does not involve errors in measuring the volume V because it takes place while the output $dV/dt$ is not present. The output of the integrator 17 is supplied to the summing means 25 by two potentiometers 61 and 63, alternately utilized by closing of a rest contact 65 or a work contact 67 of the relay 11 and displaying the value of one parameter $\lambda_1$ for exhalation and the value of other parameter $\lambda_1$ for the inhalation. The output of the amplifier 21 is supplied to the summing means 25 by two potentiometers 71 and 73 via rest contact 75 and work contact 77, respectively for the parameter $\lambda_2$ for the exhalation and the inhalation phases for the respiratory cycle. A power source of $+1V$ is connected to the summing means 25 by two potentiometers 81 and 83 via contact rest 85 and work contact 87, respectively of the relay 11, for providing the values of the parameter $\lambda_3$ at exhalation and inhalation. A differentiator-inverter circuit 69 differentiates the signal $dV/dt$ and provides an output signal $-d^2V/dt^2$ to the summing means 25 by two potentiometers 91 and 93 connected respectively to a rest contact 95 and a work contact 97, for providing the values of the parameter $\lambda_4$ at exhalation and inhalation. The summing means 25 includes a parallel circuit of a capacitor 79 of, for example 1 to 2 $\mu F$, together with a switch 89 for the filtering of the signal y.

The calibration of the system according to the present invention includes adjusting the circuit for the correction of the gain of the PTG by means of a calibrating pump as described in the copending application, the calibration of V and Pp in tension, $dV/dt$ does not have to be calibrated if the integrator has a time constant of 1 second, and for only the determination of the ventilatory intrathoracic work W, graphical calibration is effected through the operation of the oscilloscope.

The work W may also be obtained by means of a multiplier 101 supplied by the signal of the pressure Pp and by the signal of the output $dV/dt$ and followed by an integrator 102 to which the detector of the sign assures the limits of the integration:

$$W = \int_0^{VT} Pp \cdot dV = \int_0^T Pp \cdot V \cdot dt$$

and W is then read on a voltmeter 103.

For determining the values of the adjustable parameters $\lambda$, the loop of the signal y displayed on the oscilloscope is caused to be closed in a straight line by varying the potentiometers 71 and 73 for the exhalation and inhalation phases so that the values of the potentiometers correspond to the values of the parameter $\lambda_2$. Then, the straight line is caused to become horizontal by varying potentiometers 61 and 63 so as to obtain values for parameter $\lambda_1$ and the line is caused to lie upon the x axis by varying potentiometers 81 and 83 so as to obtain values for parameter $\lambda_3$. Subsequently the potentiometers 91 and 93 are varied to obtain values for parameter $\lambda_4$.

While we have shown and described only a single embodiment in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of appended claims.

What is claimed is:

1. A method of exploring the intrathoracic ventilatory mechanism of a subject comprising the steps of producing a signal y formed at least according to the equation:

$$y = \lambda_1 V + \lambda_2 \frac{dV}{dt} + Pp + \lambda_3$$

wherein V is the volume displaced in the mouth of the subject, $dV/dt$ is the first derivative of V with respect to time, Pp is the pleural pressure given by an oesophageal gas-bag, and $\lambda_1$, $\lambda_2$ and $\lambda_3$ are adjustable parameters, displaying the signal y as a function of V on an oscilloscope so that a loop is traced on the screen of the oscilloscope then successively adjusting the parameter $\lambda_2$ so that the loop traced an the oscilloscope screen closes in a straight line, adjusting the parameter $\lambda_1$ so that the straight line becomes horizontal, and adjusting the parameter $\lambda_3$ so that the horizontal straight line lies over the x axis on the oscilloscope screen whereby the adjusted values of the parameters are:

$\lambda_2$ = R-intrathoracic resistance, $\lambda_1$ = E-intrathoracic elastance, and $\lambda_3 = E(Vo - Vr)$—where $Vo$ is the pulmonary volume at the beginning of the inhalation and $Vr$ is the relaxation volume.

2. A method according to claim 1, wherein the signal y is produced according to the equation:

$$y = \lambda_1 V + \lambda_2 \frac{dV}{dt} + \lambda_4 \frac{d^2V}{dt^2} + Pp + \lambda_3$$

wherein $\lambda_4$ is an adjustable parameter and $d^2V/dt^2$ is the second derivative of $V$ with respect to time, and including the step of adjusting the parameter $\lambda_4$ after the adjustment of the parameters $\lambda_1$, $\lambda_2$ and $\lambda_3$ whereby the adjusted value of $\lambda_4 = L$ where $L$ is the intrathoracic inertance.

3. A method according to claim 1, wherein the signal y is directly produced from measurements on the subject and directly displayed on the oscilloscope.

4. A method according to claim 1, wherein measurements of the subject corresponding to the component terms of the signal y are recorded and the signal y is subsequently displayed on the screen of the oscilloscope.

5. A method according to claim 1, wherein the signal y is supplied to the vertical plate of the oscilloscope and a signal V is supplied to the horizontal plate of the oscilloscope.

6. A system for exploring the intrathoracic ventilatory mechanism of a subject, comprising pneumotachograph means for supplying a signal $dV/dt$ of the first derivative with respect to time of the volume V displaced at the mouth of the subject, integrating circuit means for receiving the signal $dV/dt$ and supplying a signal −V, first parameter means for providing an adjustable parameter signal $\lambda_1$ and providing an output signal −$\lambda_1$ V; second parameter means for providing an adjustable parameter signal $\lambda_2$ and providing an output signal $$-\lambda_2 \frac{dV}{dt},$$

third parameter means for providing an adjustable parameter signal $\lambda_3$, means for supplying a signal Pp of the pleural pressure of the subject, summing means for receiving at least the signal −$\lambda_1$ V, $$-\lambda_2 \frac{dV}{dt},$$

Pp and $\lambda_3$ for supplying a signal $$y = \lambda_1 V + \lambda_2 \frac{dV}{dt} + Pp + \lambda_3,$$

and oscilloscope means having a vertical input for receiving the signal y and a horizontal input for receiving the signal −V, whereby the signal y is displayed on the screen of the oscilloscope means as a function of V in the form of a loop, said second parameter means being adjusted so that the loop is closed in a straight line, said first parameter means being adjusted so that the straight line becomes horizontal and the third parameter means being adjusted so that the horizontal line lies on the x axis of the oscilloscope means whereby the adjusted values of said first, second and third parameter means represent $\lambda_1$ =E-intrathoracic elastance, $\lambda_2$ =R-intrathoracic resistance, and $\lambda_3$ =$E(Vo-Vr)$ where $Vo$ is the pulmonary volume at the beginning of inhalation and $Vr$ is the relaxation volume.

7. A system according to claim 6, further comprising first relay means having a plurality of rest contacts and a plurality of work contacts, and detector circuit means for detecting the sign of the signal $dV/dt$, said relay means being responsive to the sign detected by the detector means for closing the work contacts and opening the rest contacts during the inhalation of the subject.

8. A system according to claim 7, wherein said integrating circuit means includes amplifier means having a capacitor connected in a parallel therewith, and further comprising means for discharging the capacitor during inhalation of the subject.

9. A system according to claim 8, further comprising a pulse generator and a second relay means wherein said discharging means includes a switch means for triggering said pulse generator via a closed work contact of said first relay means, said pulse generator supplying pulses to said second relay means for discharging the capacitor of said integrating circuit means.

10. A system according to claim 9, wherein said pulse generator supplies pulses having a duration of approximately 50 ms.

11. A system according to claim 9, wherein said first parameter means includes first and second potentiometers connected to the output of said integrating circuit means for supplying a signal −$\lambda_1$V to said summing means, said first and second potentiometers being alternately connected to said summing means via a closed rest contact and a closed work contact of said first relay means, second amplifier means, said second parameter means includes third and fourth potentiometers connected to the output of said second amplifier means for supplying a signal $$-\lambda_2 \frac{dV}{dt}$$

to said summing means, said third and fourth potentiometers being alternately connected to said summing means via another closed rest contact and another closed work contact of said first relay means, power source means, said third parameter means including fifth and sixth potentiometers connected to the output of said power source means for supplying a signal $\lambda_3$ to said summing means, said fifth and sixth potentiometers being connected to said summing means via another closed rest contact and another closed work contact of said first relay means.

12. A system according to claim 11, wherein said power source means provides a 1 volt output signal to said fifth and sixth potentiometers.

13. A system according to claim 11, further comprising differentiator means receiving the signal $dV/dt$ for supplying a signal $-d^2V/dt^2$ of the second derivative of V with respect to time, and fourth parameter means for providing an adjustable parameter signal $\lambda_4$ and providing an output signal $$-\lambda_4 \frac{d^2V}{dt^2},$$

and said summing means receiving the signal $$-\lambda_4 \frac{d^2V}{dt^2}$$

and supplying a signal $$y = \lambda_1 V + \lambda_2 \frac{dV}{dt} + \lambda_4 \frac{d^2V}{dt^2} + Pp + \lambda_3$$

to the vertical input of said oscilloscope means, said fourth parameter means including seventh and eighth potentiometers connected to the output of said differentiator means for supplying the signal $$-\lambda_4 \frac{d^2V}{dt^2}$$

to said summing means, said seventh and eighth potentiometers being alternately connected to said summing means via another closed rest contact and closed work contact of said first relay means.

14. A system according to claim 13, wherein said summing means includes summing amplifier means having a circuit of a switch and capacitor connected in parallel therewith.

15. A system according to claim 14, wherein said capacitor of said summing means has a value of 1 to 2 $\mu F$.

16. A system according to claim 6, further comprising differentiator means receiving the signal $dV/dt$ for supplying a signal $d^2V/dt^2$ of the second derivative of V with respect to time, and fourth parameter means for providing an adjustable parameter signal $\lambda_4$ and providing an output signal $$-\lambda_4 \frac{d^2V}{dt^2},$$

and said summing means receiving the signal $$-\lambda_4 \frac{d^2V}{dt^2}$$

and supplying a signal $$y = \lambda_1 V + \lambda_2 \frac{dV}{dt} + \lambda_4 \frac{d^2V}{dt^2} + Pp + \lambda_3$$

to the vertical input of said oscilloscope means, said fourth parameter being adjusted so that the value thereof is represented by $\lambda_4 = L$ where $L$ is the intrathoracic inertance.

17. A system according to claim 16, wherein said oscilloscope means displays on the screen a loop in which the surface of the loop for the value zero of the parameters $\lambda_1, \lambda_2, \lambda_3$ and $\lambda_4$ is a measure of the intrathoracic ventilatory work W.

18. A system according to claim 6, wherein said oscilloscope means displays on the screen a loop in which the surface of the loop for the value zero of the parameters $\lambda_1, \lambda_2,$ and $\lambda_3$ is a measure of the intrathoracic ventilatory work W.

19. A system according to claim 6, further comprising multiplying means for receiving the signal $Pp$ and $dV/dt$ and providing a multiplied signal $$Pp \cdot \frac{dV}{dt},$$

and integrator means for integrating the multiplied signal in accordance with the sign of the signal $dV/dt$, and a voltmeter responsive to the output of the integrator means for displaying the intrathoracic ventilatory work W.

* * * * *